United States Patent [19]

Geremakis

[11] Patent Number: 4,770,658
[45] Date of Patent: Sep. 13, 1988

[54] JOINT PROSTHESIS

[75] Inventor: Perry A. Geremakis, Warsaw, Ind.
[73] Assignee: Zimmer, Inc., Warsaw, Ind.
[21] Appl. No.: 44,672
[22] Filed: May 1, 1987
[51] Int. Cl.⁴ .............................................. A61F 2/34
[52] U.S. Cl. ......................................... 623/22; 623/23
[58] Field of Search .................... 623/22, 23; 403/122, 403/135, 140; 128/92 E

[56] References Cited

U.S. PATENT DOCUMENTS

| | | | |
|---|---|---|---|
| 3,210,105 | 10/1965 | Vogt | 287/87 |
| 3,545,797 | 12/1970 | Korecky | 287/87 |
| 3,818,512 | 10/1974 | Shersher | 3/1 |
| 4,241,463 | 12/1980 | Khovaylo | 3/1.913 |
| 4,318,627 | 3/1982 | Morin | 403/133 |
| 4,380,090 | 4/1983 | Ramos | 3/1.912 |
| 4,619,658 | 10/1986 | Pappas | 623/22 |
| 4,650,491 | 3/1987 | Parchinski | 623/22 |
| 4,718,911 | 1/1988 | Kenna | 623/22 |

FOREIGN PATENT DOCUMENTS 0053794  6/1982  European Pat. Off. .
1057833  5/1954  Fed. Rep. of Germany .
1276271 10/1961  France .

Primary Examiner—Richard J. Apley
Assistant Examiner—J. Welsh
Attorney, Agent, or Firm—Paul David Schoenle

[57] ABSTRACT

A joint prosthesis is provided wherein an outer shell includes a liner to define an articulating interface with a head of a hip stem. A lock ring cooperates with the outer shell and the liner to oppose withdrawal of the head from the liner, and the lock ring is carried by the outer shell to permit insertion of the head during assembly.

5 Claims, 2 Drawing Sheets

JOINT PROSTHESIS

A joint prosthesis is provided to replace a diseased or dysfunctional human joint. In a hip joint, for example, a femur terminates at the proximal end in a head of generally spherical shape for articulation in an acetabulum. With a hip prosthesis a femoral component is secured via suitable means such as bone cement or a press fit within the femoral intramedullary canal such that a head on the femoral component is disposed in cooperation with the acetabulum.

In U.S. Pat. No. 4,619,658 issued to Michael J. Pappas et al, a spherical cup is provided to cooperate with a spherical head of a femoral component. The spherical cup defines a first articulating outer surface cooperating with the acetabulum while a liner within the cup defines a second articulating inner surface cooperating with the spherical head. In order to retain the spherical head within the liner and cup, a split lock ring is connected to the liner in opposition to the cup to form an interference opposing withdrawal of the spherical head. The lock ring is formed by a split collar with a retaining ring carried on the outer surface of the split collar. When the spherical head is pulled outwardly from the cup, forces transmitted from the spherical head to the split collar bias the latter in an outward direction. Although the cup and retaining ring oppose radial expansion of the collar, the split in the collar is designed to provide for radial expansion in contradistinction to the purpose of the retaining ring. Moreover, with the split collar in engagement with the rotatable head, the head is constantly biasing the split collar to separate from the liner via a direct frictional engagement.

Additional split lock rings are illustrated in U.S. Pat. Nos. 4,241,463; 4,230,415; 3,797,128; German Pat. No. 659900; and Japanese Disclosure Document No. 49,97-155.

The present invention includes a joint prosthesis with a liner fixedly secured to an outer shell and cooperating therewith to define a recess for receiving a lock ring at an open end of the outer shell. The lock ring comprises a solid annular member without any split. In a first position the lock ring is carried by the outer shell to form a unitary assembly accommodating insertion of a spherical head into the shell and liner. In a second position the lock ring tightly engages the liner and outer shell to maintain the liner in overlapping relation to the spherical head and oppose withdrawal of the spherical head from the liner and outer shell.

It is an advantage of the present invention that the lock ring is solid in construction so that radial expansion of the portion of the liner in tight engagement with the lock ring is substantially eliminated. Moreover, the lock ring is carried by the outer shell in the first and second positions to provide a unitary assembly for easy entrapment of the head within the shell. In the first and second position, the lock ring remains spaced from the spherical head at all times so that frictional articulation is limited to the liner.

In the drawings accompanying specification,

Figure 1:
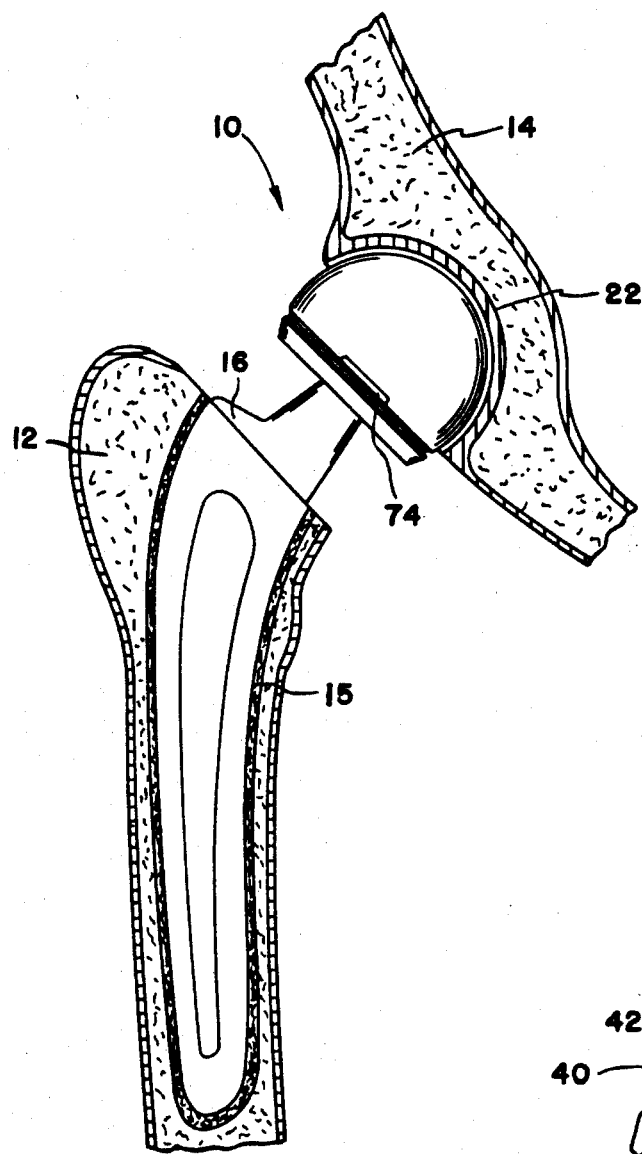
FIG. 1 is a side view of the joint prosthesis of the present invention.

A joint prosthesis 10 is surgically implanted between a femur 12 and an acetabulum 14 to provide for universal articulation between the femur 12 and the acetabulum 14. In general the femoral head (not shown) is resected to expose the femoral intramedullary canal 15. A stem 16 of joint prosthesis 10 is inserted into the intramedullary canal for fixation thereto by a press fit or the application of bone cement. The stem 16 terminates at the proximal end in a spherical head 18 (shown in phantom in FIG. 2) and a cup assembly 20 is carried on the spherical head 18 for engagement and articulation with the acetabulum 14 via a bone cavity 22 on the acetabulum 14.

Figure 2:
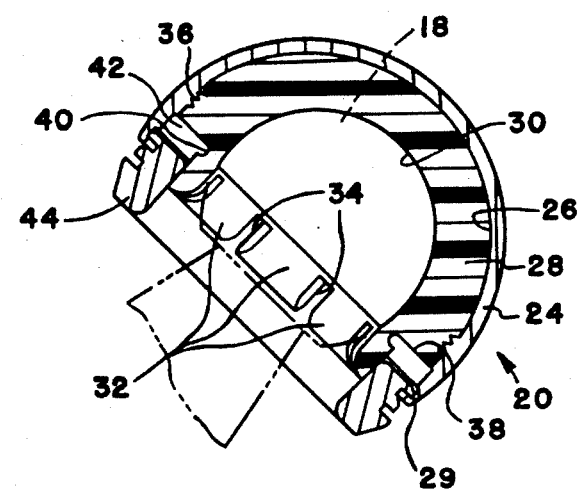
FIG. 2 is a cross sectional view of the joint prosthesis of FIG. 1 with the stem of FIG. 1 shown in phantom for clarity to illustrate the liner.

Turning to FIG. 2, the cup assembly 20 includes a spherical outer shell 24 forming a socket 26 to receive a liner 28 via an open end 29. The liner 28 also forms a socket 30 substantially matching the contour of the spherical head 18. The liner 28 includes a plurality of fingers 32 with slots 34 therebetween. In order to retain the liner within the outer shell 24 a plurality of ridges 36 extend inwardly to form a interference opposing withdrawal of the liner from the shell 24. Near the ridges 36 the liner 28 includes a transverse shoulder 38 extending radially from the plurality of fingers 32. A relief 40 between the shoulder 38 and the fingers enhances the flexibility of the fingers as described hereinafter. A recess 42 is formed at the open end 29 of the shell between the shell 24, the shoulder 38 and the plurality of fingers 32 in order to receive a lock ring 44 in the recess 42. The lock ring 44 cooperates with the plurality of fingers in a first position to permit insertion of the head 18 into the socket 30 while in a second position the lock ring 44 cooperates with the plurality of fingers 32 to oppose withdrawal of the head 18 from the socket 30.

Figure 3:
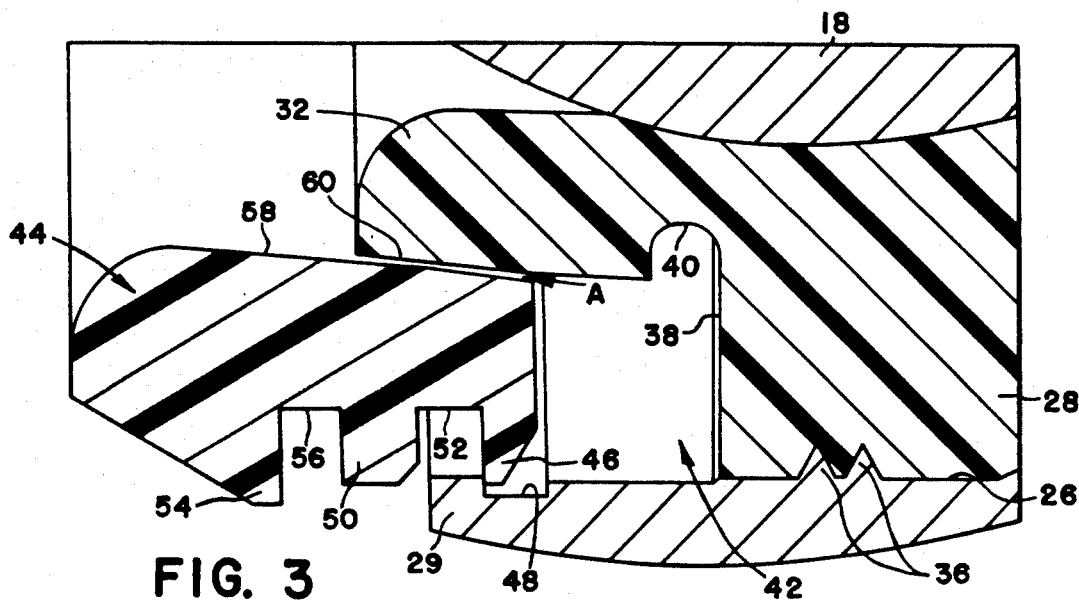
FIG. 3 is an enlarged view of the circumscribed portion of FIG. 2.

In FIGS. 2 and 3 the lock ring 44 is shown in the first position. Turning to FIG. 3, a first lip 46 is disposed within an annular groove 48 adjacent the open end 29. A second lip 50 is spaced from the first lip by a channel 52 and a third lip 54 is spaced from the second lip by another channel 56. With the first lip 46 disposed in the groove 48, the lock ring is loosely connected to the shell 24, to define a small clearance A between an inner surface 58 on the lock ring 44 and an outer surface 60 on each of the plurality of fingers 32. Preferably, both surfaces 58 and 60 include a taper of about four degrees (4°). In the first position the plurality of fingers are expandible to take up the clearance A when the head 18 is pushed into the socket 30.

Figure 4:
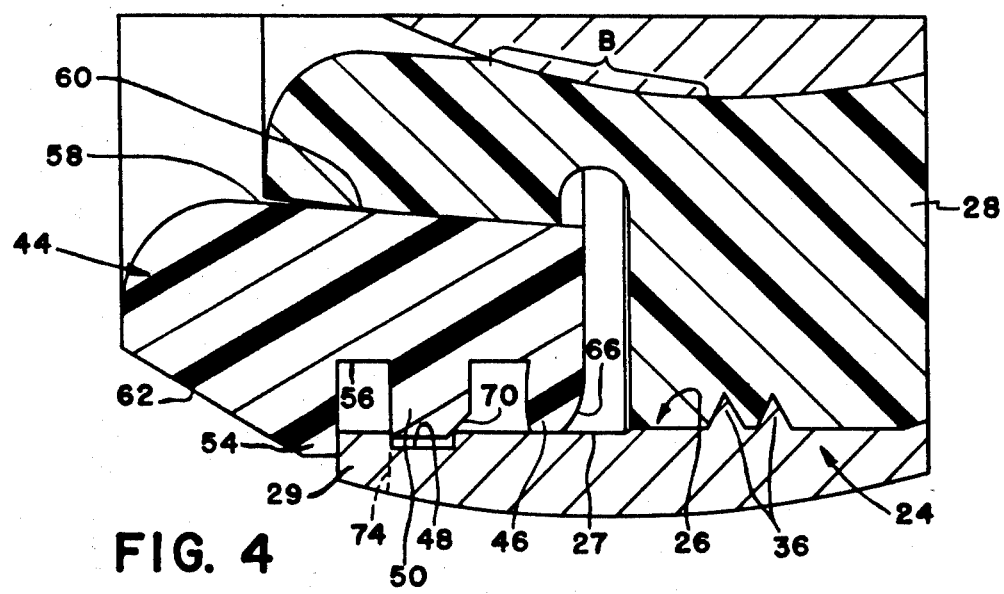
FIG. 4 is a view similar to FIG. 3 showing the lock ring in the second position.
Figure 5:
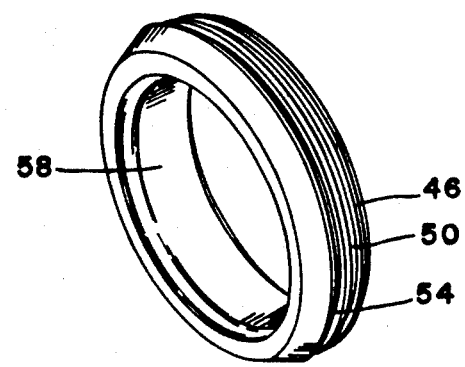
FIG. 5 is a perspective view of the lock ring.

In FIG. 4 the lock ring 44 has been moved to its second position wherein the second lip 50 is disposed within the annular groove 48 and the first lip 46 is tightly engaging a flat wall 27 of socket 26 to retain the lock ring 44 concentrically disposed within the socket 26. The third lip 54 is chamfered on its outer surface 62 to substantially match the outer spherical contour of shell 24. In the second position, the inner surface 58 of the lock ring 44 is in tight engagement with the outer surface 60 of the plurality of fingers 32 to retain the latter around the head 18 throughout region B which is outside the diametral center line of head 18 within socket 30. Region B forms an interference with the head 18 to oppose withdrawal of the head 18 from the socket 30 in the second position. In order to accommodate movement of the first lip 46 from the first position to the second position, the thickness of the first lip 46 is sufficiently thin to permit slight deformation of the first lip in the second position. Moreover, the first lip includes a chamfer 66 at its leading edge to enhance the deformability of the first lip as it moves from groove 48 to flat wall 27. In the same manner during assembly of the lock ring 44 to the shell 24, the first lip 46 is forced into the open end 29 of the shell to locate the first lip 46 in groove 48. In contrast to the first lip 46, the second lip 50 is sufficiently thick to provide a robust lock or catch with the end wall of the groove 48 when the second lip 50 is disposed in the groove 48, and a chamfer 70 on the leading edge enables the second lip to extend into the groove 48 across the entire width of the latter. The chamfer 70 also facilitates movement of the second lip from the first position outside the socket 26 to the second position within the socket 26 past the open end 29. Viewing FIGS. 3 and 4, the first lip 46 is thinner than the second lip 50 and the chamfer 66 generates a larger taper than the chamfer 70.

The deformation of the first lip 46 to tightly engage the wall 27 and the disposition of the second lip within the groove 48 provide separate retention forces maintaining the lock ring 44 in its second position. Although the first lip 46 is tightly engaging the wall 27 to oppose any radial expansion of the plurality of fingers 32, the solid construction of the lock ring is primarily responsible for opposing radial expansion of the plurality of fingers 32 in the second position and the lock ring engages the plurality of fingers 32 over a substantial length extending axially on both sides of the lip 50.

In order to disassemble the lock ring 44 from its second position, the shell 24 is provided with one or more cut outs 74, see FIG. 1, in alignment with the channel 56 to enable a releasing tool to bias the lock ring to move from the second position to the first position.

In view of the foregoing description, it is seen that the lock ring 44 is conveniently carried within the shell 24 to provide a unitary assembly in both positions. The lock ring 44 is solid without any split to provide a strong lock around the plurality of fingers in opposition to radial expansion of the latter when forces attempt to separate the head 18 from the liner and shell.

We claim:

1. A joint prosthesis for restoring articulation comprising a cup disposed adjacent a first skeletal member and a stem disposed adjacent a second skeletal member which is movable with respect to the first skeletal member, the stem including a spherical head for insertion into the cup, the cup comprising an outer shell with a socket for receiving a liner, the liner cooperating with the spherical head to define an articulating interface therebetween, and a lock ring cooperating with the outer shell and the liner to selectively retain the spherical head within the liner, the lock ring comprising a solid annular member defining a first position in cooperation with the outer shell to permit insertion of the spherical head into the cup while the lock ring is retained in connection with the outer shell, the lock ring being movable to a second position relative to the outer shell to oppose withdrawal of the spherical head from the outer shell, the wall of the outer shell socket including an annular groove and the lock ring including a first lip projecting outwardly and disposed in the annular groove in the first position and a second lip projecting outwardly and disposed in the annular groove in the second position, and the second lip defines a thickness which is greater in dimension than for the first lip in order to provide a robust structure opposing separation between the second lip and the annular groove.

2. The joint prosthesis of claim 1 in which the first lip is less rigid than the second lip so as to be slightly deformable to permit easy connection of the lock ring to the outer shell in the first position.

3. The joint prosthesis of claim 1 in which the first lip defines an interference friction fit with the outer shell to oppose movement of the lock ring from the second position to the first position, and the second lip extends into the annular groove to abut an end wall thereof to further oppose movement of the lock ring from the second position to the first position.

4. A joint prosthesis for restoring articulation between a pair of associated skeletal members comprising a stem secured to one of the members and terminating in a head disposed within a cup assembly for engagement with the other member, the cup assembly including a shell cooperatively engaging the other member, a liner engaging the head and a lock ring of solid construction cooperating with the liner to oppose withdrawal of the head from the liner, the liner defining a socket for receiving the head and a plurality of fingers which are deformable to partially surround the head, the plurality of fingers cooperate with the shell to form a recess at an open end of the shell to receive the lock ring in the recess, the open end of the shell defining a groove facing the plurality of fingers and receiving a portion of the lock ring to retain the latter in the recess so that the lock ring remains spaced from the head and engages a substantial length of the plurality of fingers whereby the plurality of fingers are rigidly held to partially surround the head when the lock ring is retained in the groove, the locking ring defining a pair of lips projecting radially outwardly with a channel between the pair of lips, one of the pair of lips engaging the shell at the open end and the other lip defining the portion of the lock ring received within the groove, the shell defining a cut out in alignment with the channel when the one lip is in engagement with the shell so that a releasing tool may engage the lock ring at the channel via the cut out to move the lock ring relative to the recess.

5. The joint prosthesis of claim 4 in which the lock ring includes at least one lip extending radially outwardly to extend into the groove and the one lip is disposed at an intermediate location on the lock ring to provide for engagement between the lock ring and the plurality of fingers on both sides of the one lip.

* * * * *

UNITED STATES PATENT AND TRADEMARK OFFICE
CERTIFICATE OF CORRECTION

PATENT NO. : 4,770,658
DATED : September 13, 1988
INVENTOR(S) : Geremakis, et al.

It is certified that error appears in the above—identified patent and that said Letters Patent is hereby corrected as shown below:

Title page:

Inventor: Perry A. Geremakis, Warsaw, IN should read

Inventor: Perry A. Geremakis, Warsaw, IN
          Roy Hori, Warsaw, IN
          George E. Simpson, Fort Wayne, IN Signed and Sealed this Seventh Day of March, 1989

*Attest:*

DONALD J. QUIGG

*Attesting Officer*        *Commissioner of Patents and Trademarks*